United States Patent [19]

Wemple et al.

[11] Patent Number: 4,885,386
[45] Date of Patent: Dec. 5, 1989

[54] PROCESS FOR THE SYNTHESIS OF 3-CHLORO-2,4,5-TRIFLUOROBENZOIC ACID

[75] Inventors: James N. Wemple; Gregory L. Karrick; Floyd G. Spence, all of Holland, Mich.

[73] Assignee: Warner-Lambert Company, Morris Plains, N.J.

[21] Appl. No.: 264,296

[22] Filed: Oct. 28, 1988

[51] Int. Cl.$^4$ ............................................. C07C 51/363
[52] U.S. Cl. ..................................... 562/493; 562/456; 560/47
[58] Field of Search ................... 560/47; 562/456, 493

[56] References Cited

U.S. PATENT DOCUMENTS 4,359,428 11/1982 Jacobs et al. ........................ 562/456
4,439,620 3/1984 Klauke et al. ........................ 560/47
4,771,054 9/1988 Domagala et al. .................. 514/312
4,782,179 11/1988 Hirota et al. ........................ 562/456

FOREIGN PATENT DOCUMENTS 183129 6/1986 European Pat. Off. ............ 514/312
195316 9/1986 European Pat. Off. ............ 514/312
3631906 3/1988 Fed. Rep. of Germany ...... 562/456

Primary Examiner—James H. Reamer
Attorney, Agent, or Firm—Francis J. Tinney

[57] ABSTRACT

An improved process for the preparation of 3-chloro-2,4,5-trifluorobenzoic acid is described which involves reaction of a diester of 3,4,5,6-tetrafluoro-1,2-benzenedicarboxylic acid with a substituted amine to afford 3-amino-2,4,5-trifluorobenzoic acid followed by subsequent conversion of the amio intermediate into 3-chloro-2,4,5-trifluorobenzoic acid.

12 Claims, No Drawings

PROCESS FOR THE SYNTHESIS OF 3-CHLORO-2,4,5-TRIFLUOROBENZOIC ACID

BACKGROUND OF THE INVENTION

8-Chloro-1-cyclopropyl-6,7-difluoro-1,4-dihydro-4-oxo-3-quinolinecarboxylic acid is a key intermediate in the preparation of 7-amino-substituted-8-chloro-1-cyclopropyl-6-fluoro-1,4-dihydro-4-oxo-3-quinolinecarboxylic acids described in U.S. Pat. No. 4,771,054. These 7-amino substituted-8-chloro-1-cyclopropyl-6-fluoro-1,4-dihydro-4-oxo-3-quinolinecarboxylic acids are useful as antibacterial agents.

8-Chloro-1-cyclopropyl-6,7-difluoro-1,4-dihydro-4-oxo-3-quinolinecarboxylic acid may be, in turn, prepared by a series of steps starting with 3-chloro-2,4,5-trifluorobenzoic acid.

3-Chloro-2,4,5-trifluorobenzoic acid is not commercially available since it is difficult to synthesize. Thus, synthetic methods for preparing 3-chloro-2,4,5-trifluorobenzoic acid are disclosed in DE No. 36 31 906 and European Pat. Application Nos. 183129 and 195316. However, all the previous methods suffer the disadvantages of requiring multistep procedures which also involve a potentially hazardous nitration step.

The object of the present invention is an improved process for preparing 3-chloro-2,4,5-trifluorobenzoic acid by using a novel synthetic scheme.

The present method utilizes inexpensive starting materials and proceeds in fewer steps and higher yields compared to the previous methods.

SUMMARY OF THE INVENTION

Accordingly, a first aspect of the present invention is an improved process for the preparation of a compound of Formula I

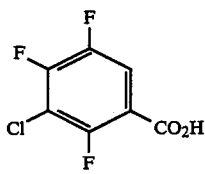

which comprises
(a) reacting a compound of Formula IV

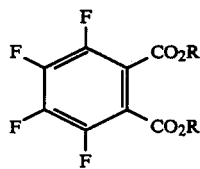

wherein R is alkyl of from one to eight carbon atoms with
(1) a compound of Formula

$R_1NH_2$ wherein $R_1$ is tertiary butyl, tertiary pentyl, benzyl or para methoxybenzyl in a polar aprotic solvent at about 0° C. to about 80° C. and
(2) reacting the resulting intermediate of Formula III

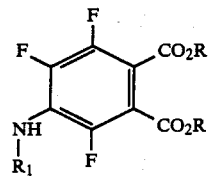

wherein R and $R_1$ are as defined above, in situ with an acid at about 70° C. to about 140° C. to afford a compound of Formula II; and

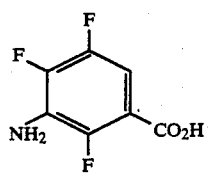

(b) finally reacting a compound of Formula II in a conventional manner to give a compound of Formula I.

A second aspect of the present invention is an improved process for the preparation of the compound of Formula II

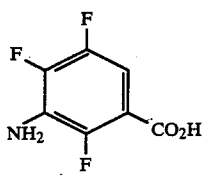

which comprises
(a) reacting a compound of Formula IV

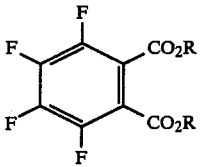

wherein R is alkyl of from one to eight carbon atoms with
(1) a compound of Formula

$R_1NH_2$ wherein $R_1$ is tertiary butyl, tertiary pentyl, benzyl or para methoxybenzyl in a polar aprotic solvent at about 0° C. to about 80° C. and
(2) reacting the resulting intermediate of Formula III

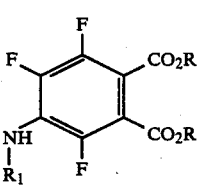

wherein R and $R_1$ are as defined above, in situ with an acid at about 70° C. to about 140° C. to afford a compound of Formula II.

DETAILED DESCRIPTION OF THE INVENTION

The term "alkyl" contemplated by the present invention means a straight or branched hydrocarbon group having from one to eight carbon atoms and includes, for example, methyl, ethyl, n-propyl, isopropyl, n-butyl, isobutyl, tertiary-butyl, n-pentyl, n-hexyl, n-heptyl, n-octyl, and the like.

The process of the present invention is a new, improved, economical and commercially feasible method for preparing 3-chloro-2,4,5-trifluorobenzoic acid. The process of the present invention is outlined in the following scheme:

SCHEME I

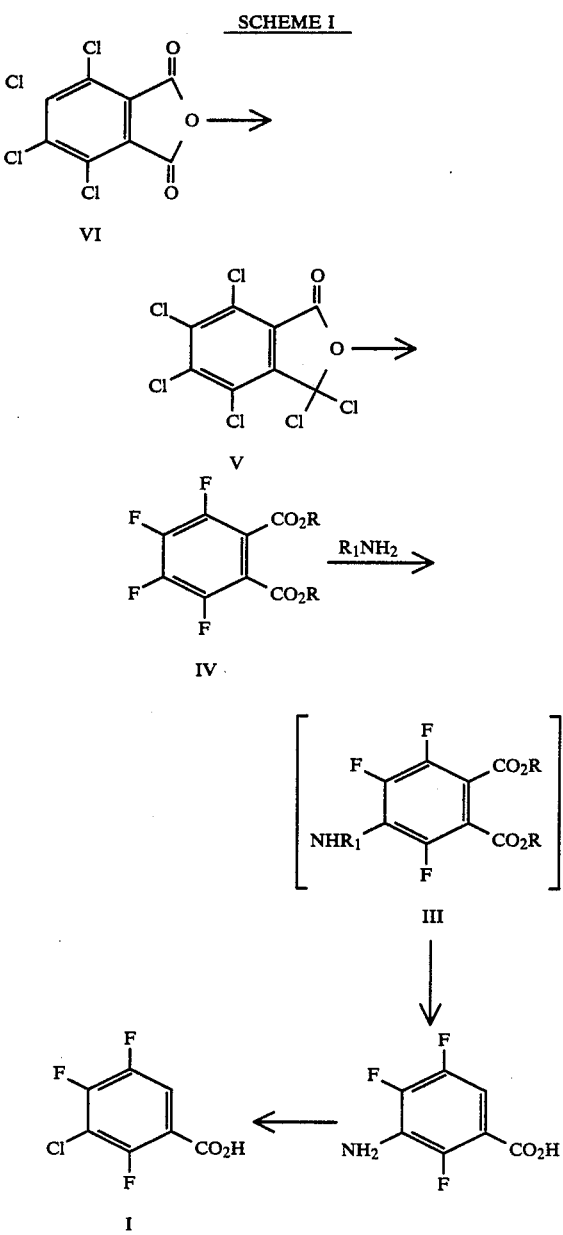

4,5,6,7-Tetrachloro-1,3-isobenzofurandione (tetrachlorophthalic anhydride) (VI) is converted in 90% yield to 3,3,4,5,6,7-hexachloro-1-[3H]isobenzofuranone (perchlorophthalide) (V) as described previously (A. Kirpal and H. Kunze. *Chemische Berichte*, 62B, pages 2102 to 2106 (1929) and U.S. Ser. No. 860,728). Treatment of perchlorophthalide (V) with anhydrous potassium fluoride in sulfolane at 140°–160° C. followed by the addition of a compound of Formula R—OH, wherein R is alkyl of from one to eight carbon atoms in the presence of a base such as, for example, triethylamine or potassium carbonate, using a modification of the methodology described previously (U.S. Ser. No. 860,728) affords a compound of Formula IV wherein R is as defined above. A compound of Formula IV is reacted with an excess of two or more equivalents of a compound of Formula $R_1NH_2$, wherein $R_1$ is tertiary butyl, tertiary pentyl, benzyl or para methoxybenzyl, in a polar, aprotic solvent such as, for example, dimethylsulfoxide, sulfolane, dimethylformamide, dimethylacetamide, N-methylpyrrolidone, acetonitrile, and the like at about 0° C. to about 80° C. for about one to about ten hours to afford a compound of Formula III. In place of an excess of a compound of Formula $R_1NH_2$ one equivalent of a compound of formula $R_1NH_2$, wherein $R_1$ is as defined above, and one equivalent or more of a tertiary amine such as, for example, triethylamine, ethyldiisopropylamine, 1,8-diazabicyclo[5.4.0]undec-7-ene (DBU), and the like, may be used as a base to neutralize the hydrofluoric acid liberated in the reaction. Preferably, the reaction is carried out by treating the compound of Formula

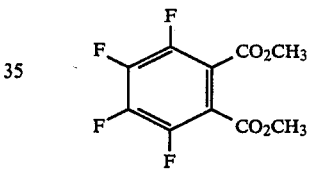

with an excess of a compound of Formula $R_1NH_2$, wherein $R_1$ is tertiary butyl or tertiary pentyl, in dimethylsulfoxide or sulfolane at about room temperature for about three hours. The reaction mixture is diluted with water and the compound of Formula III extracted into a nonpolar organic solvent such as heptane in order to remove the polar aprotic solvent, dimethylsulfoxide or sulfolane. After stripping the heptane the compound of Formula III is treated with an aqueous acid such as, for example, hydrochloric acid, sulfuric acid, hydrobromic acid, phosphoric acid, and the like, at about 70° C. to about 140° C. for about 12 to about 48 hours to afford the compound of Formula II. Preferably, the reaction is carried out by refluxing a compound of Formula III in 36% aqueous hydrochloric acid solution for about 20 hours. The compound of Formula II is converted in a conventional manner to a compound of Formula I. Thus, the compound of Formula II is combined with sodium nitrite and the resulting solid mixture added to an aqueous solution of cupric chloride in aqueous hydrochloric acid at about 0° C. to about 90° C. for about 0.5 to about five hours to afford, after extraction with an inert, water immiscible solvent such as, for example, toluene, xylene, diethyl ether, n-butyl ether, and the like, the compound of Formula I. Preferably, the reaction is carried out by adding the compound of Formula II and sodium nitrite to an aqueous solution of cupric chloride and a 36% aqueous hydrochloric acid solution at about 15° C. to about 25° C. and extracted with diethyl ether. Alternatively, the compound of Formula II and cupric chloride are added to hydrochloric acid and then an aqueous solution of sodium nitrite is added over about one hour while the temperature is about 0° C. to about 5° C. and then the mixture stirred about two hours to afford after extraction with an inert, water immiscible solvent such as, for example, toluene, xylene, diethyl ether, n-butyl ether, and the like, the compound of Formula I. Preferably, the reaction is carried out by adding the compound of Formula II and cupric chloride to a 3% aqueous hydrochloric acid solution followed by addition to this of an aqueous solution of sodium nitrite over about one hour while the reaction is kept about 0° C. to about 5° C. and extracted with toluene.

Thus, the present method proceeds in a four-part process, starting with the inexpensive 4,5,6,7-tetrachloro-1,3-isobenzofurandione (tetrachlorophthalic anhydride) to afford in high yield 3-chloro-2,4,5-trifluorobenzoic acid.

U.S. Pat. No. 4,771,054, European Pat. Application Nos. 0183129 and 0195316 disclose the use of 3-chloro-2,4,5-trifluorobenzoic acid in the preparation of antibacterial agents.

The following examples are illustrative to show the present process, the preparation of starting materials, and the use of 3-chloro-2,4,5-trifluorobenzoic acid obtained by the present process to prepare the key intermediate, 8-chloro-1-cyclopropyl-6,7-difluoro-1,4-dihydro-4-oxo-3-quinolinecarboxylic acid, in the synthesis of 7-amino-substituted-8-chloro-1-cyclopropyl-6-fluoro-1,4-dihydro-4-oxo-3-quinolinecarboxylic acid antibacterial agents.

EXAMPLE 1

3,4,5,6-Tetrafluoro-1,2-benzenedicarboxylic acid, dimethyl ester

Method A:

Anhydrous potassium fluoride (63 g) and tetramethylenesulfone (85 ml)) are combined and the mixture heated to 150° C. Perchlorophthalide (Example A) (24 g) is added over a 30-minute period. The mixture is then stirred at 150°-155° C. for 3.5 hours. It is cooled to 100° C. and toluene (100 ml) is added followed by methanol (4.75 g). The mixture is then cooled to 10° C. and triethylamine (14.95 g) slowly added. The mixture is stirred at 25° C. overnight. The next day it is filtered and the residue washed with toluene (3×100 ml). Heptane (200 ml) is added to the combined toluene filtrate. This solution is extracted with a 5% aqueous solution of hydrochloric acid (3×100 ml) followed by water (3×100 ml). The organic layer is concentrated to a solid (17.6 g), which is recrystallized from toluene (5 ml), and heptanes (15 ml). The crystals are collected and washed with heptanes (2×10 ml) and vacuum dried to give 3,4,5,6-tetrafluoro-1,2-benzenedicarboxylic acid, dimethyl ester (13.6 g, 72%); mp 70°-72° C., GC (95.9%).

Method B:

Anhydrous spray-dried potassium fluoride (63 g) is added to a 500-ml flask followed by tetramethylenesulfone (87 ml). The mixture is heated with stirring to 155° C. Perchlorophthalide (Example A) (24 g) is added in portions over 25 minutes at 145°-155° C. The resulting mixture is then stirred at 140°-150° C. for three hours and 15 minutes. The mixture is cooled to 10° C. and methanol (4.85 g) is added. Triethylamine (14.95 g) is then added over 20 minutes with ice bath cooling in order to maintain the reaction temperature between 10°-20° C. The resulting mixture is allowed to stir overnight at room temperature. The next day it is filtered and the salts washed with toluene (3×100 ml). The combined toluene filtrates are diluted with heptanes (200 ml) and extracted with a 5% aqueous solution of hydrochloric acid (3×75 ml) and then water (2×100 ml). The organic layer is concentrated to a solid (17.0 g). This is recrystallized from toluene (10 ml) and heptanes (10 ml), and after cooling in an ice bath the crystals are collected and washed with heptanes (3×10 ml) and vacuum dried to give 3,4,5,6-tetrafluoro-1,2-benzenedicarboxylic acid, dimethyl ester (12.2 g, 65%); mp 70°-72° C., GC (97.2%).

EXAMPLE 2

3-Amino-2,4,5-trifluorobenzoic acid

Method A:

3,4,5,6-Tetrafluoro-1,2-benzenedicarboxylic acid, dimethyl ester (Example 1), 2.66 g, is treated with 8 g of dimethylsulfoxide and the mixture is warmed to dissolve the solid. The solution is cooled in an ice bath and 2.65 g of tertiary-pentylamine is added. The resulting solution is then stirred at room temperature for three hours, 50 ml of water added, and the solution extracted with heptanes (2×30 ml). The combined heptane extract is extracted with a 5% aqueous solution of hydrochloric acid (2×4 ml) and concentrated to give 4-[(1,1-dimethylpropyl)amino]-3,5,6-trifluoro-1,2-benzenedicarboxylic acid, dimethyl ester as an oil. Hydrochloric acid (36% aqueous solution), 20 ml, is added to this oil and the resulting mixture is heated at reflux for 20 hours. The solution is concentrated to 4-5 ml and then diluted with water (20 ml). Cooling gave crystals which are collected and vacuum dried to give 1.2 g of 3-amino-2,4,5-trifluorobenzoic acid (63%); mp 133°-136° C.; GC (97.9%); HPLC (94%).

Method B:

3,4,5,6-Tetrafluoro-1,2-benzenedicarboxylic acid, dimethyl ester (Example 1), 13.5 g, is dissolved in a mixture of toluene (10 ml) and tetramethylene sulfone (70 ml) by warming. The solution is cooled to 25° C. Tertiary-butylamine (24.71 g) is added and the solution is stirred at ambient temperature for six hours. Water (100 ml) is added and the solution is extracted with heptanes (3×100 ml). The combined heptane extract is then extracted first with a 5% aqueous solution of hydrochloric acid (100 ml), then with demineralized water (100 ml). The heptane portions are combined and concentrated to give dimethyl 4-t-butylamino-3,5,6-trifluoro-1,2-benezenedicarboxylate as an oil. Concentrated (36%) hydrochloric acid solution (100 ml) is added to the oil and the mixture is refluxed for 20 hours. The mixture is cooled to 25° C. and a 10% sodium hydroxide solution (216 g) is added to adjust the pH to 1.5, causing a precipitate to form. The precipitate is collected by filtration, washed with water (3×50 ml), dried by suction, and then vacuum dried for 64 hours at 45° C. to yield the title compound (6.23 g, 64.2%); mp 136°-138° C.

Method C:

Perchlorophthalide (Example A), 19.2 g, anhydrous spray-dried potassium fluoride, 49.6 g, and dry tetramethylene sulfone, 70 ml, are stirred together under an atmosphere of dry nitrogen at 148°-155° C. for 3.5 hours. The mixture is cooled to 100° C. and treated with toluene (100 ml). It is further cooled to 25° C. and a solution prepared by mixing anhydrous methanol (3.79 g) and anhydrous triethylamine (11.96 g) is added dropwise over five minutes while maintaining the temperature between 20° C. and 30° C. with a water bath. The mixture is stirred at 20°-25° C. for two hours and then filtered and the solids washed with toluene (100 ml). The filtrates are concentrated by stripping off toluene under vacuum at 60°-65° C. The residual solution of crude 3,4,5,6-tetrafluoro-1,2-benzenedicarboxylic acid, dimethyl ester in tetramethylene sulfone and residual toluene is treated with t-butylamine (24.71 g), added dropwise at 20°-25° C. The mixture is stirred under nitrogen at 25°-28° C. for six hours. Water (100 ml) is added and the solution extracted with heptanes (3×100 ml). The combined heptane extract is washed first with a 5% aqueous solution of hydrochloric acid (100 ml), then with water (2×100 ml), and then concentrated to give dimethyl 4-t-butylamino-3,5,6-trifluoro-1,2-benzenedicarboxylate as an oil. Demineralized water (50 ml) and a 36% aqueous solution of hydrochloric acid (50 ml) are added to the oil and the mixture refluxed for 25-40 hours. The mixture is reduced to a solid by stripping off water and hydrochloric acid under vacuum. The solid is treated with demineralized water (100 ml) at 100° C. for 30 minutes and the hot mixture filtered. The filtrate is again reduced to a solid by stripping off water under vacuum. The solid is dissolved in water (41 ml) at 100° C. Cooling the resulting solution to 20° C. over three hours gives crystals which are collected by filtration, washed with demineralized water (3×20 ml), dried by suction, and then dried under vacuum at 45° C. for 20 hours to yield the title compound (6.04 g, 56.2%); mp 127°-129° C. Recrystalization from toluene gives a 70% recovery of material with mp 137.0°-138.5° C.

EXAMPLE 3

3-Chloro-2,4,5-trifluorobenzoic acid

Method A:

A solid mixture of 0.52 g of 3-amino-2,4,5-trifluorobenzoic acid (Example 2) and 0.33 g of sodium nitrite is added in portions to a solution of 3 g of cupric chloride in 9 ml of water and 0.5 g of a 36% aqueous solution of hydrochloric acid. The resulting mixture is allowed to stir at 15°-25° C. for 1.5 hours and then additional water (25 ml) is added. Stirring is continued another hour at 25° C. and then 20 ml of diethyl ether is added. The layers are separated and the aqueous layer extracted with 20 ml of diethyl ether. The combined organic extracts are extracted with 5 ml of a 36% aqueous solution of hydrochloric acid and then concentrated on the rotary evaporator to give 0.45 g of 3-chloro-2,4,5-trifluorobenzoic acid as a tan solid; gas chromatography (GC) (98.8%); high performance liquid chromatography (HPLC) (84.8%); (a portion of the 3-chloro-2,4,5-trifluorobenzoic acid was recrystallized from heptanes; mp 109°-111° C.).

Method B:

3-Amino-2,4,5-trifluorobenzoic acid (Example 2), 0.52 g, and 3 g of cupric chloride are added to 10 ml of a 3% aqueous solution of hydrochloric acid and the mixture is stirred with ice bath cooling. A solution of 0.32 g of sodium nitrite in 4 ml of water is added to the reaction mixture in portions over a one-hour period while maintaining the reaction at 0°-5° C. The ice bath is then removed and the mixture is stirred for two hours at room temperature. Toluene, 20 ml, and 15 ml of water are added with stirring. The layers are separated and the aqueous layer extracted with 20 ml of toluene. The combined toluene extracts are extracted with 4 ml of a 36% aqueous solution of hydrochloric acid and then concentrated to a solid under reduced pressure to give 0.48 g (83%) of 3-chloro-2,4,5-trifluorobenzoic acid as a tan solid; GC (98.4%); HPLC (89.2%); recrystallization from heptanes gives 0.40 g (70%) of 3-chloro-2,4,5-trifluorobenzoic acid; mp 109°-111° C.

EXAMPLE 4

8-Chloro-1-cyclopropyl-6,7-difluoro-1,4-dihydro-4-oxo-3-quinolinecarboxylic acid Step A: Preparation of 3-Chloro-2,4,5-trifluorobenzoyl chloride A solution of 9.4 g (45 mmol) of 3-chloro-2,4,5-trifluorobenzoic acid (Example 3), oxalyl chloride, 7.6 g (60 mmol), 3 drops of dimethylformamide, and 100 ml of dichloromethane is stirred at room temperature for three hours. The solvent and excess oxalyl chloride are evaporated on the steam bath, and the residue is distilled at 121°-123° C. at 30 mm Hg to give 2.9 g of the title compound.

Step B: Preparation of Ethyl $\beta$-(3-chloro-2,4,5-trifluorophenyl)-$\beta$-oxopropionate To a mixture of 2.64 g (20 mmol) of malonic acid monoethyl ester, 0.10 g (catalytic amount) of dipyridyl, and 50 ml of dry tetrahydrofuran at −30° C. is added 13 ml of n-butyllithium (1.55 M, 20.2 mmol) at a rapid rate. When addition is complete, the solution is warmed to −5° C., and another 13 ml of n-butyllithium (1.55 M, 20.2 mmol) is added dropwise until a pale pink color persists for ten minutes. The suspension is then cooled to −78° C. To this mixture is added a solution of 2.3 g (10 mmol) of 3-chloro-2,4,5-trifluorobenzoyl chloride in 3 ml of dry tetrahydrofuran. The reaction mixture is stirred at −78° C. for one hour, then warmed to −35° C. and poured into a mixture of ice (50 g) and 6 N hydrochloric acid (4 ml). This solution is extracted with dichloromethane, and the extracts are washed with water, 5% aqueous sodium bicarbonate, dilute hydrochloric acid, and water. The organic phase is dried over magnesium sulfate, filtered, and concentrated to give 2.5 g of the title compound as an orange solid.

Step C: Preparation of Ethyl 2-(3-chloro-2,4,5-trifluorobenzoyl)-3-ethoxyacrylate A mixture of 2.3 g (8.2 mmol) of ethyl $\beta$-(3-chloro-2,4,5-trifluorophenyl)-$\beta$-oxopropionate, 2 ml of triethyl orthoformate, and 20 ml of acetic anhydride is refluxed for 2½ hours. The reaction mixture is cooled to room temperature and concentrated to give 2.7 g of the title compound as a red oil.

Step D: Preparation of Ethyl 2-(3-chloro-2,4,5-trifluorobenzoyl)-3-cyclopropylaminoacrylate A solution of 2.7 g (8.0 mmol) of ethyl 2-(3-chloro-2,4,5-trifluorobenzoyl)-3-ethoxyacrylate, 0.46 g (8.0 mmol) of cyclopropylamine, and 40 ml of dry t-butanol is stirred at 45° C. for 2½ hours. The mixture is cooled to room temperature and used without purification in the next step.

Step E: Preparation of Ethyl 8-chloro-1-cyclopropyl-6,7-difluoro-1,4-dihydro-4-oxo-3-quinolinecarboxylate To a solution of ethyl 2-(3-chloro-2,4,5-trifluorobenzoyl)-3-cyclopropylaminoacrylate in 40 ml of dry t-butanol is added a slurry of 1.20 g (10.7 mmol) of potassium t-butoxide in 20 ml of dry t-butanol. The reaction mixture is stirred at 6° C. for eight hours, then cooled to room temperature and concentrated. The residue is dissolved in chloroform, washed with water, dried over magnesium sulfate, filtered, and concentrated to give a pale brown solid. The crude product is purified by silica gel chromatography, and eluted with 80:20 chloroform-:ethyl acetate to give 1.2 g of the title compound.

Step F: Preparation of 8-Chloro-1-cyclopropyl-6,7-difluoro-1,4-dihydro-4-oxo-3-quinoline carboxylic acid A suspension of 1.1 g (3.36 mmol) of ethyl 8-chloro-1-cyclopropyl-6,7-difluoro-1,4-dihyiro-4-oxo-3quinolinecarboxylate, 10 ml of 6 N hydrochloric acid, and 1 ml of tetrahydrofuran is refluxed for 2½ hours. The mixture is cooled to room temperature, and the solids are filtered, washed with water and diethyl ether, and dried to give 0.76 g of the title compound as a white powder; mp 189°–191° C.

EXAMPLE 5

7-[(3-amino)-1-pyrrolidinyl]-8-chloro-1-cyclopropyl-6-fluoro-1,4-dihydro-4-oxo-3-quinolinecarboxylic acid Step A: Preparation of 7-[(3-t-Butoxycarbonylamino)-1-pyrrolidinyl]-8-chloro-1-cyclopropyl-6-fluoro-1,4-dihydro-4-oxo-3-quinolinecarboxylic acid A suspension of 0.92 g (4.94 mmol) of 1,1-dimethylethyl(3-pyrrolidinyl)carbamate (Example B), 0.74 g (2.47 mmol) of 8-chloro-1-cyclopropyl-6,7-difluoro-1,4-dihydro-4-oxo-3-quinolinecarboxylic acid (Example 4), 0.62 g (6.14 mmol) of triethylamine, and 20 ml of acetonitrile is refluxed for three hours and then cooled to room temperature. The solid which precipitates is filtered, washed with acetonitrile and diethyl ether, and dried to give 1.2 g of the title compound; mp 175°–178° C.

Step B: Preparation of 7-[(3-Amino)-1-pyrrolidinyl]-8-chloro-1-cyclopropyl-6-fluoro-1,4-dihydro-4-oxo-3-quinolinecarboxylic acid To a suspension of 0.90 g (1.93 mmol) of 7-[(3-t-butoxycarbonylamino)-1-pyrrolidinyl]-8-chloro-1-cyclopropyl-6-fluoro-1,4-dihydro-4-oxo-3-quinlinecarboxylic acid in 15 ml of ethanol is added 5 ml of 6 N hydrochloric acid, and the mixture is stirred at 60° C. for one hour. Once the solids have dissolved, the solution is cooled to room temperature and concentrated to a gold oil. The oil is dissolved in 1N sodium hydroxide and acidified to pH 7.4. The solid that precipitates is filtered and dried to give 0.43 g of the title compound; mp 241°–242° C.

PREPARATION OF STARTING MATERIALS

EXAMPLE A 3,3,4,5,6,7-Hexachloro-1-[3H]-isobenzofuranone (Perchlorophthalide)

4,5,6,7-Tetrachloro-1,3-isobenzofurandione (tetrachlorophthalic anhydride), 1.35 kg, phosphorus pentachloride, 1.30 kg, and phosphoryl chloride, 240 ml, are combined and the mixture heated to 133° C. at which point phosphoryl chloride began refluxing. The mixture is allowed to reflux with stirring for 38 hours. More phosphorus pentachloride (100 g) is added and refluxing continued another 27 hours. The solution is distilled initially at atmospheric pressure. After most of the phosphoryl chloride has been removed, distillation is continued at 10 torr while the pot temperature is increased to 143° C. When no additional distillate is produced, the liquid is cooled to 115° C. and xylenes (500 ml) are added followed by isooctane (5.2 L) in portions over a 30-minute period. The solution is cooled with stirring overnight. The crystals are collected and washed with heptanes (1 L) and dried under vacuum to give 1.17 kg of perchlorophthalide (72%); mp 136°–138° C.

EXAMPLE B 1,1-Dimethylethyl (3-pyrrolidinyl)carbamate

Step A: Preparation of 1,1-dimethylethyl [1-(phenylmethyl)-3-pyrrolidinyl]carbamate A solution of 77.0 g (0.44 mol) of 1-(phenylmethyl)-3-pyrrolidineamine [Journal of Medicinal Chemistry 24, 1229 (1981)], 440 ml (0.44 mol) 1.0 N sodium hydroxide, and 600 ml of tertiary butyl alcohol is treated dropwise with 98.2 g (0.45 mol) of di-tertiary butyl dicarbonate. The reaction is stirred at room temperature for 18 hours and the solvent removed in vacuo. The residue is partitioned between diethyl ether and water. The aqueous layer is reextracted with diethyl ether, the combined diethyl ether extracts are washed with water, dried (MgSO$_4$), filtered, and evaporated on a steam bath replacing the diethyl ether with petroleum ether. The crystals which form are removed by filtration, washed with diethyl ether/petroleum ether (1:1), and dried in vacuo to give 84.8 g of 1,1-dimethylethyl [1-(phenylmethyl)-3-pyrrolidinyl]carbamate; mp 114°–115° C. A second crop (16.7 g) is obtained by concentrating the filtrate.

Step B: Preparation of 1,1-Dimethylethyl (3-pyrrolidinyl)carbamate

A mixture of 27.6 g (0.1 mol) of 1,1-dimethylethyl[1-(phenylmethyl)-3-pyrrolidinyl]carbamate, 1.0 g of 20% Palladium on carbon and 140 ml of methanol is shaken in an atmosphere of hydrogen at about 50 psi and room temperature for 24 hours. The catalyst is removed by filtering through Celite, and the filtrate is concentrated in vacuo to give 18.4 g of 1,1-dimethylethyl (3-pyrrolidinyl)carbamate which solidifies upon standing.

We claim:

1. A process for the preparation of a compound of Formula I

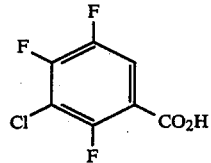

which comprises:
(a) reacting a compound of Formula IV

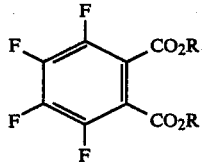

wherein R is alkyl of from one to eight carbon atoms with
(1) a compound of Formula

R$_1$NH$_2$ wherein R$_1$ is tertiary butyl, tertiary pentyl, benzyl, or para methoxybenzyl in a polar aprotic solvent at about 0? C. to about 80? C. and
(2) reacting the resulting intermediate of Formula III

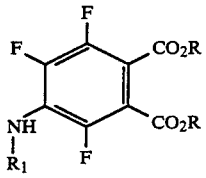

wherein R and R₁ are as defined above, in situ with an aqueous acid at about 70° C. to about 140° C. to afford a compound of Formula II

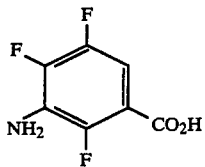

(b) finally reacting a compound of Formula II with sodium nitrite and the resulting solid mixture added to an aqueous solution of cupric chloride in aqueous hydrochloric acid at about 0° C. to about 90° C. for about 0.5 to about five hours to give after extraction with an inert, water immiscible solvent a compound of Formula I.

2. A process for the preparation of the compound of Formula II

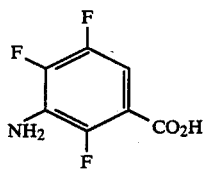

which comprises
(a) reacting a compound of Formula IV

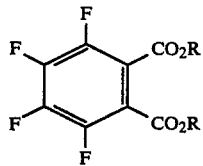

wherein R is alkyl of from one to eight carbon atoms with
(1) a compound of Formula

R₁NH₂ wherein R₁ is tertiary butyl, tertiary pentyl, benzyl or para methoxybenzyl in a polar aprotic solvent at about 0° C. to about 80° C. and
(2) reacting the resulting intermediate of Formula III

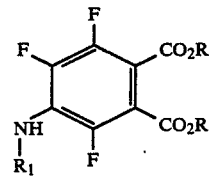

wherein R and R₁ are as defined above, in situ with an aqueous acid at about 70° C. to about 140° C. to afford a compound of Formula II.

3. A process according to claim 2, wherein the polar aprotic solvent in step (a)(1) is selected from the group consisting of dimethylsulfoxide, sulfolane, dimethylacetamide, dimethylformamide, N-methylpyrrolidone and acetonitrile.

4. A process according to claim 2, wherein the acid in step (a)(2) is selected from the group consisting of hydrochloric acid, sulfuric acid, hydrobromic acid, and phosphoric acid.

5. A process according to claim 3, wherein the polar aprotic solvent is selected from the group consisting of dimethylsulfoxide and sulfolane.

6. A process according to claim 4 wherein the acid is hydrochloric acid.

7. A process according to claim 2 wherein R is methyl.

8. A process according to claim 2 wherein R₁ is tertiary butyl or tertiary pentyl.

9. A process according to claim 2, wherein the temperature in step (a)(1) is about 0° C. to about 25° C.

10. A process according to claim 2, wherein the temperature in step (a)(2) is about 100° C. to about 120° C.

11. A process according to claim 8, wherein R₁ is tertiary pentyl.

12. A process according to claim 5 wherein the polar aprotic solvent is dimethylsulfoxide.

UNITED STATES PATENT AND TRADEMARK OFFICE
CERTIFICATE OF CORRECTION

PATENT NO. : 4,885,386
DATED : December 5, 1989
INVENTOR(S) : James N. Wemple, et al.

It is certified that error appears in the above—identified patent and that said Letters Patent is hereby corrected as shown below:

In column 10, line 66, delete "0? C. to about 80? C." and insert --0°C. to about 80°C.--

Signed and Sealed this

Twenty-third Day of October, 1990

Attest:

HARRY F. MANBECK, JR.

Attesting Officer  Commissioner of Patents and Trademarks